United States Patent [19]

Colescott et al.

[11] 4,055,524

[45] Oct. 25, 1977

[54] SYNTHESIS OF PEPTIDES

[75] Inventors: Robert L. Colescott, Bourbonnais; Emil Kaiser, Chicago; Charles D. Bossinger, Olympia Fields; Paul I. Cook, Kankakee, all of Ill.

[73] Assignee: Armour Pharmaceutical Company, Phoenix, Ariz.

[21] Appl. No.: 603,771

[22] Filed: Aug. 11, 1975

Related U.S. Application Data

[63] Continuation-in-part of Ser. No. 441,770, Feb. 12, 1974, Pat. No. 3,915,949.

[51] Int. Cl.$^2$ .................... C08L 89/00; C07C 103/52
[52] U.S. Cl. ................................ 260/8; 260/112.5 R
[58] Field of Search .............................. 260/112.5 R, 8

[56] References Cited

PUBLICATIONS

Schroder, E. and K. Lubke, "The Peptides", vol. 1, Academic Press, New York, 1965, pp. 77–97.
J. M. Stewart and J. D. Young, "Solid Phase Peptide Synthesis," Freeman and Co., San Francisco, 1969, pp. 13–20.

*Primary Examiner*—Delbert R. Phillips
*Attorney, Agent, or Firm*—Richard R. Mybeck; Frank T. Barber; Carl C. Batz

[57] ABSTRACT

Resin peptides useful in the preparation of peptides having biological activity, and particularly such resin peptides containing ®-CH$_2$-Phe-Glu at one end of an amino acid chain, ® being the resin and Phe and Glu being the residues of the amino acids phenylalanine and glutamic acid; and processes for the preparation of such resin peptides. Resin peptides are disclosed which contain amino acid chains identical with the amino acid chains of natural peptides having biological activity. Other resin peptides are disclosed which contain amino acid chains in which the amino acid residues differ in kind and sequence from amino acid chains of natural biologically active peptides but from which peptides having biological activity may be derived.

13 Claims, No Drawings

SYNTHESIS OF PEPTIDES

This application is a continuation-in-part of our application Ser. No. 441,770 filed Feb. 12, 1974, now U.S. Pat. No. 3,915,949.

This invention relates to the synthesis of peptides and particularly resin peptides which are useful in the production of biologically active peptides. The invention involves such peptides as new compounds and also processes by which they may be produced.

BACKGROUND

It has long been known that certain natural biologically active substances can be obtained from the glands of animals and the substances so obtained utilized in the treatment of deficiencies of the human body. One such substance is the adrenocorticotropic hormone, commonly called ACTH, which for many years has been obtained from the pituitary glands of animals, particularly porcine and bovine pituitary glands.

The burden of having to collect the relatively small pituitary glands of animals at the time the animals are slaughtered, the limitation to the quantity of such glands which can be collected and the extensive purification procedures which are required to produce peptides which can be administered to humans, are indeed formidable disadvantages to the preparation of natural peptide hormones from animal glands. For many years the art has eagerly awaited the discovery of practical methods and compounds which enable the commercial synthesis of such peptides as ACTH from other than animal sources. To our knowledge there have been no such compounds or methods prior to the discoveries of the present invention.

The human adrenocorticotropic hormone (ACTH) has been identified as having the following structure:

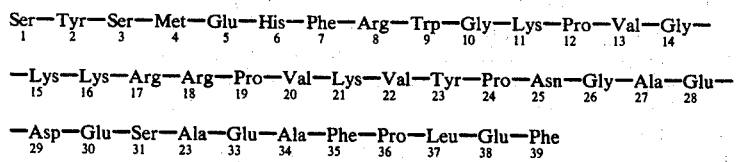

where the abbreviations Phe, Glu, Leu, etc. stand for the different amino acid groupings in the peptide chain and the numbers represent the positions of the amino acid groups in the chain according to accepted nomenclature. See the article by Riniker et al, in *Nature New Biology*, 235, 114-115, (1972).

It is a principal object of this invention to discover intermediate resin peptides from which biologically active peptides may be derived, particularly peptides with adrenocorticotropic hormone activity, and to provide effective processes for the commercial production of such peptides. Other more specific objects will become apparent as this specification proceeds.

We are aware of disclosures of certain laboratory methods for the synthesis of certain peptides of relatively short amino chain lengths. These include an article by R. B. Merrifield entitled "Solid Phase Peptide Synthesis. I. The Synthesis of a Tetrapeptide" at pages 2149 to 2154 in Vol. 85 of Journal of the American Chemical Society (1963) and a book entitled "Solid Phase Peptide Synthesis" by John W. Stewart and Janis D. Young published by W. H. Freeman and Company of San Francisco, California, but find in these publications no disclosures of resin peptides having amino groups of the kind and in the sequence involved in the present invention.

DESCRIPTION OF INVENTION

Our total synthesis involves many reactions by which many new intermediate resin peptides are formed and we will proceed with the description step by step, giving the structural formula, the general description and specific examples as we proceed.

In general, we utilize a solid phase synthesis in which the insoluble polystyrene resin is chloromethylated. We couple to the resin first phenylalanine, then glutamic acid and the other amino acids of the chain, in prescribed sequence, using a system of protection and deprotection of the active amine and carboxyl groups. Following the coupling of the last amino acid in the chain the resin is cleaved from the peptide chain and the remaining protective groups removed.

Preparation of Insoluble Resin

The chloromethylation of the resin is described by the following structural formula:

®, in the above formula, is the insoluble polystyrene resin which is manufactured in bead form by the catalytic polymerization of styrene and divinyl benzene. This resin is chloromethylated using chloromethyl methyl ether and stannic chloride catalyst.

The reaction is specifically illustrated by the following example.

EXAMPLE 1

One Kg of 2% divinylbenzene crosslinked polystyrene resin 200-400 mesh was washed with three 2 liter portions of methylene chloride. Fine particles were removed by draining the methylene chloride off the bottom each time. The resin was washed with two liters of the following solvents by suspension, stirring for 10 minutes and filtration on a sintered glass Buchner: Two portions tetrahydrofuran, 2 portions water, 1 portion normal sodium hydroxide, 2 portions water, 2 portions dimethylformamide, 2 portions dioxane and 3 portions methanol. This washed resin was dried under vacuum at 60° C.

Five hundred grams of this washed polystyrene resin was stirred with 5 liters of chloromethyl methyl ether at room temperature and then the temperature was lowered to 0°-5° C. with an ice-water bath. Seventy-five grams of anhydrous stannic chloride in 925 ml ice-cold chloromethyl methyl ether was added and the mixture stirred in the ice-bath for 2 hours. The resin was filtered on a sintered glass Buchner and then washed with 2 liter portions of the following solvents: 25% water in dioxane, 25% two normal hydrochloric acid in dioxane, water and twice with methanol. The washed resin was dried under vacuum at 45°-50° C.. By this method the usual chloride content is between 0.7 to 1.0 milli-equivalent per gram.

Phenylalanine Esterification to the Polystyrene Resin

By our synthesis phenylalanine is first bonded to the polystyrene resin. This is described by the following formula:

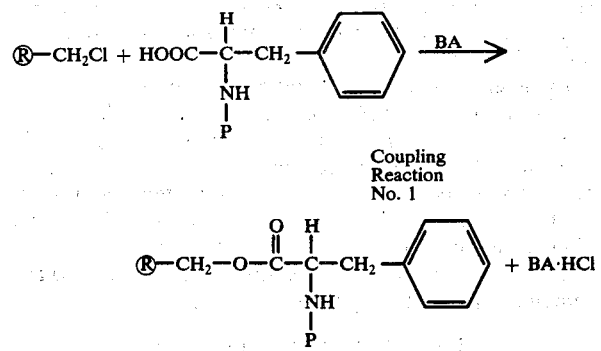

Coupling Reaction No. 1 where ®  is polystyrene resin, BA is a suitable base such as triethylamine, diisopropylamine, diisopropylethylamine, or alkali metal salt, and P is an amino protective group which preferably is tertiary-butyloxycarbonyl (BOC) but may be amyloxycarbonyl (AMOC) or o-nitrophenylsulfenyl (NPS).

As illustrated by the above formula the tertbutyloxy-l-phenylalanine is attached to the chloromethylated resin in the presence of an acid acceptor. This reaction is demonstrated by the following specific Example 2.

EXAMPLE 2

Fifty grams of chloromethylated polystyrene resin, prepared as above described, with a chlorine content of 0.74 milli-equivalent (meq) per gram (37 meq chlorine) and 19.6 grams BOC-l-phenylalanine (74 meq) stirred in 150 ml of absolute ethyl alcohol and then 9.77 ml of triethylamine (72 meq) was added and the mixture refluxed with stirring for 24 hours. The mixture was cooled, filtered on a sintered glass Buchner and washed on the Buchner with 500 ml portions of the following solvents: 2 times with 3A denatured alcohol, 2 times with dioxane, 2 times with 3A denatured alcohol, 2 times with water, 2 times with methanol. The resin was dried under vacuum at 40°–54° C.. Nitrogen analysis will show values varying from about 0.50 to 0.70 meq per gram. When the BOC protecting group was removed with trifluoroacetic acid as hereinafter described and the resin titrated to determine the available terminal amine group, this sample was found to approximate 0.38 meq per gram.

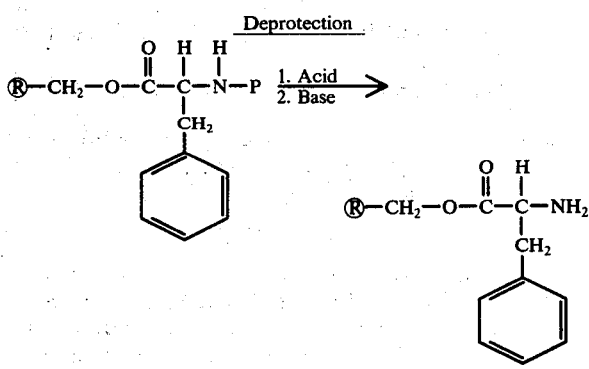

This resulting resin peptide is designated Compound No. 1.

The deprotection of the amine function of the phenylalanine is accomplished by the removal of the protecting group using a suitable acid such as trifluoracetic acid or hydrochloric acid. The resulting amine salt is then neutralized by treatment with a strong organic base. A specific example of this procedure is given in the following Example 3.

EXAMPLE 3

A 25 gram sample of the BOC-phenylalanine resin as prepared by Example 2 was placed in the reaction vessel of a peptide synthesizer. The sample was washed twice with 125 ml portions of methylene chloride for two minutes each. 125 ml of 50% trifluroacetic acid in methylene chloride was added and the mixture reacted for 30 minutes. After filtration the resin was washed with three 125 ml portions of methylene chloride, 2 portions of methanol and 3 portions of chloroform, each was being of 2 minute duration. Neutralization was accomplished by a 5 minute reaction with 125 ml of a 10% solution of triethylamine and chloroform. The resin was then washed 3 times with 125 ml of chloroform and 3 times with 125 ml of methylene chloride.

Coupling of Glutamic Acid

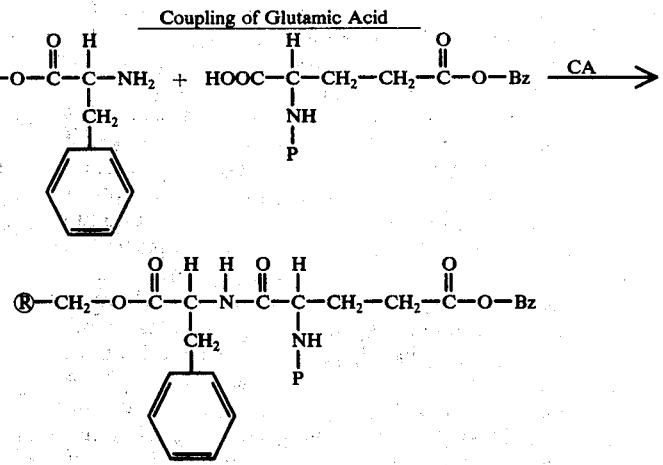

In the above formula CA is a coupling agent which preferably is dicyclohexylcarbodiimide (DCC) but may be any coupling agent which forms peptide bonds, such as diimides, azides, active esters, and anhydrides. The term Bz is benzyl or a benzyl derivative such as, for example, p-methoxybenzyl, p-chlorobenzyl, p-nitrobenzyl, or benzhydryl. The symbols ®, BA, P, CA and Bz are to be taken as having the meanings above defined wherever they appear in this specification and claims.

Since the formula as above given begins to be cumbersome we may rewrite the formula of the reaction product in the following manner:

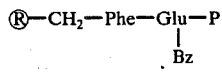

where Phe stands for the phenylalanine residue, Glu stands for the glutamic acid residue and P and Bz are as previously defined. This simplified nomenclature will be utilized in the description of all subsequent reactions.

In carrying out the reaction the P, Bz and glutamic acid may be combined as in BOC-l-γ-benzylglutamate and this added to the deprotected phenylalanine resin and the coupling promoted by addition of DCC. This coupling is then followed by deprotection just as explained in connection with the phenylalanine resin peptide. The resulting product following deprotection bears the formula:

(Compound No. 2)

We believe that this resin peptide was made for the first time by our invention, and that this is an important link in the synthesis of the hormone, ACTH.

Further, we believed it is important that the coupling reaction be complete and have found the Ninhydrin test described by E. Kaiser, R. Colescott, C. Bossinger and P. Cook, the inventors herein, in *Anal. Biochem.* 34, 595–98 (1970) to be applicable to determine when the coupling reaction is sufficiently complete. If the Ninhydrin test is negative we may proceed to the deprotection of the resin peptide and go on to the following coupling reaction. If this test is positive we repeat the coupling step until the Ninhydrin test result is finally negative.

Following are specific examples of the coupling of glutamic acid:

EXAMPLE 4

To the deprotected phenylalanine resin with 10.7 meq of amine group was added a solution of 15 millimoles (approx. 50% excess) of BOC-l-γ-benzylglutamate in 100 ml of methylene chloride. After two minutes a solution of 15 meq of dicyclohexylcarbodiimide (DCC) was added and the mixture agitated for 45 minutes. The product was filtered and washed twice each with 125 ml portions of chloroform and methylene chloride. The Ninhydrin test was performed on a 3–5 mg sample of resin peptide reaction product and found to be negative. This resin was then deprotected as was described in Example 3.

EXAMPLE 4A

Two grams phenylalanine resin was deprotected and neutralized as previously described. Three millimoles of NPS-l-γ-benzyl glutamate, dissolved in 25 ml of methylene chloride, was added followed by three millimoles of dicyclohexylcarbodiimide. The mixture was agitated for one hour, filtered and washed with two portions of methylene chloride, two portions of methanol and three portions of methylene chloride.

EXAMPLE 4B

In place of NPS in Example 4A we may substitute AMOC in the same meq amounts and substantially the same results may be expected.

EXAMPLE 4C

In place of BOC-l-γ-benzylglutamate we may use 15 millimoles of BOC-l-γ-p-bromobenzylglutamate, and the reaction carried through in the manner set forth in Example 4. In this case we obtain the product in which the Bz group is p-bromobenzyl. After deprotection and neutralization we obtain Compound 2 the same as obtained in Example 4.

EXAMPLE 4D

In Example 4 the Bz group is benzyl. Either p-methoxybenzyl, p-chlorobenzyl, p-nitrobenzyl or benzylhydryl may be substituted for the benzyl group in BOC-l-γ-benzylglutamate, and the procedure carried out as set forth in Example 4 to obtain a reaction product in which the Bz group is p-methoxybenzyl, p-chlorobenzyl, p-nitrobenzyl, or benzhydryl. After deprotection and neutralization we obtain in each case Compound 2, the same as obtained in Example 4.

The following Table 1 lists in sequence the amino acids attached at each of reactions 2 to 39 indicating the position in chain in which the attachment is made and listing the reactant used with the preferred carboxyl protecting groups.

Table I

| Reaction Number | Position Number | Amino Acid Being Attached | Amino Acid Group With Preferred Protectants |
|---|---|---|---|
| 2 | 38 | glutamic acid | BOC-*l*-γ-benzyl glutamate |
| 3 | 37 | leucine | BOC-*l*-leucine hydrate |
| 4 | 36 | proline | BOC-*l*-proline |
| 5 | 35 | phenylalanine | BOC-*l*-phenylalanine |
| 6 | 34 | alanine | BOC-*l*-alanine |
| 7 | 33 | glutamic acid | BOC-*l*-γ-benzyl glutamate |
| 8 | 32 | alanine | BOC-*l*-alanine |
| 9 | 31 | serine | BOC-O-benzyl-*l*-serine |
| 10 | 30 | glutamic acid | BOC-*l*-γ-benzyl glutamate |
| 11 | 29 | aspartic acid | BOC-*l*-β-benzyl-aspartate |
| 12 | 28 | glutamic acid | BOC-*l*-γ-benzyl glutamate |
| 13 | 27 | alanine | BOC-*l*-alanine |
| 14 | 26 | glycine | BOC-glycine |
| 15 | 25 | asparagine | BOC-*l*-asparagine-p-nitrophenylester |
| 16 | 24 | proline | BOC-*l*proline |
| 17 | 23 | tyrosine | BOC-*l*-tyrosine (20% dimethylformamide for solubility) |
| 18 | 22 | valine | BOC-*l*-valine |
| 19 | 21 | lysine | BOC-2-chlorocarbobenzyloxy-*l*-lysine (10% dimethylformamide for solubility) |
| 20 | 20 | valine | BOC-*l*-valine |
| 21 | 19 | proline | BOC-*l*-proline |
| 22 | 18 | arginine | BOC-*l*-tosylarginine (20% dimethylformamide for solubility) |
| 23 | 17 | arginine | BOC-*l*-tosylarginine (20% dimethylformamide for solubility) |
| 24 | 16 | lysine | BOC-2-chlorocarbobenzyloxy-*l*-lysine (10% dimethyl formamide for solubility) |
| 25 | 15 | lysine | BOC-2-chlorocarbobenzyloxy-*l*-lysine |

Table I-continued

| Reaction Number | Position Number | Amino Acid Being Attached | Amino Acid Group With Preferred Protectants |
|---|---|---|---|
| 26 | 14 | glycine | (10% dimethylformamide for solubility) BOC-glycine |
| 27 | 13 | valine | BOC-*l*-valine |
| 28 | 12 | proline | BOC-*l*-proline |
| 29 | 11 | lysine | BOC-2-chlorocarbobenzyloxy-*l*-lysine (10% dimethylformamide for solubility) |
| 30 | 10 | glycine | BOC-glycine |
| 31 | 9 | tryptophan | BOC-*l*-tryptophan (5% dimethylformamide for solubility) |
| 32 | 8 | arginine | BOC-*l*-tosylarginine (20% dimethylformamide for solubility) |
| 33 | 7 | phenylalanine | BOC-*l*-phenylalanine |
| 34 | 6 | histidine | BOC-im-carbobenzyloxy-*l*-histidine |
| 35 | 5 | glutamic acid | BOC-*l*-γ-benzylglutamate |
| 36 | 4 | methionine | BOC-*l*-methionine |
| 37 | 3 | serine | BOC-O-benzyl-*l*-serine |
| 38 | 2 | tyrosine | BOC-*l*-tyrosine (20% dimethylformamide for solubility) |
| 39 | 1 | serine | BOC-O-benzyl-*l*-serine |

As was described in connection with the attachment of glutamic acid in reaction No. 2, each succeeding reaction to attach another amino acid group involves the same procedure in which the resin peptide previously prepared is coupled with another amino acid group under condition of protection, then the coupled peptide is deprotected and neutralized. More specifically, the following steps may in the case of each reaction be as follows:

Coupling:
15 millimoles of the appropirate BOC-amino acid (0.43 equivalent excess in 100 ml of methylene chloride)

15 millimoles of dicyclohexylcarbodiimide (coupling agent) in 15 ml of methylene chloride - 40 minutes reaction time 2× 125 ml - chloroform washes - 2 minutes each
2× 125 ml - methylene chloride - 2 minutes each
Deprotection:
2× 125 ml - methylene chloride washes - 2 minutes each 50% trifluoroacetic acid in methylene chloride - 5 minutes 125 ml 50% trifluoroacetic acid in methylene chloride - 25 minutes 125 ml 3× 125 ml - methylene chloride washes - 2 minutes each 2× 125 ml - methanol washes - 2 minutes each 3× 125 ml - chloroform washes - 2 minutes each
Neutralization:
2× 125 ml - 10% triethylamine in chloroform - 5 minutes each 4× 125 ml - chloroform washes - 2 minutes each The procedures for making the coupling, the deprotection and neutralization steps in each of reactions 3 to 39 may be the same as already described in connection with reaction No. 2 except for the variances set forth in the following description.

As previously stated the Compound No. 2 which is the result of reaction No. 2 (after deprotection and neutralization) is:

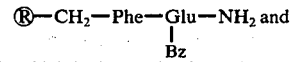

Compound No. 3, which is the result of reaction No. 3, is:

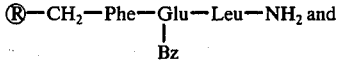

Compound No. 4, the result of reaction No. 4, is:

and, Compound No. 5, the result of reaction No. 5, is:

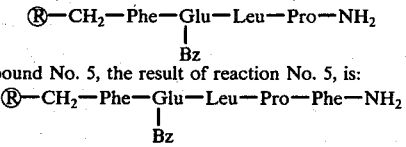

This pattern continues until the attachment of Asn at the 25th position. At this position the coupling agent DCC cannot be used because of a side reaction that destroys some of the asparagine so at this position the amino acid is coupled as an "active ester".

The deprotected resin peptide is agitated with an active ester of asparagine such as p-nitrophenyl ester, ortho-nitrophenyl ester or penta-chlorophenyl ester.

This coupling is demonstrated more specifically by the following Example 5.

EXAMPLE 5

The resin peptide represented by Compound No. 14 obtained as a result of reaction No. 14 (after deprotection and neutralization) was washed with three portions of dimethylformamide for two minutes each. Three millimoles of BOC-l-asparagine-p-nitrophenyl ester dissolved in 15 ml of dimethylformamide was shaken with the resin for 16 hours, then washed with three portions of dimethylformamide, three portions of methanol and three portions of methylene chloride.

EXAMPLE 5A

In place of the p-nitrophenyl ester of Example 5 either ortho-nitrophenyl ester or penta-chlorophenyl ester may be substituted, and the reaction carried out as set forth in Example 5 to accomplish the coupling of asparagine.

The coupling at position 25, by the active ester procedure is followed by the usual deprotection and neutralization and this results in the resin peptide compound No. 15 and is represented by the following formula:

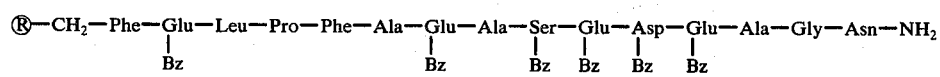

In reactions Nos. 17 and 38, at positions Nos. 23 and 2 respectively, where tyrosine is attached we prefer to use no protection on the phenolic hydroxyl of the tyrosine but may use a benzyl or benzyl derivative protector. The symbol Y is defined to mean no protection or benzyl or benzyl derivative.

To illustrate, the formula for Compound No. 17 formed as a result of reaction No. 17, we give the following structural formula:

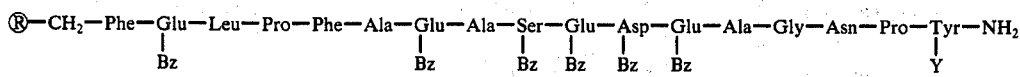

In reaction No. 19, position No. 21, where lysine is attached, we prefer to use as the epsilon amine protection agent 2-chlorocarbobenzyloxy (Cl-CBZ) but may also use carbobenzyl (CBZ), bromocarbobenzyloxy, 2,4-dichlorocarbobenzyloxy, or trifluoroacetyl (TFA).

We use the symbol V to indicate that the epsilon protection agent is one of these named groups. This V protection agent is used also for attachment of lysine in each of reactions Nos. 24, 25 and 29 at positions Nos. 16, 15 and 11 respectively. To illustrate, the structural formula for Compound No. 19 formed as a result of reaction No. 19 is given as follows:

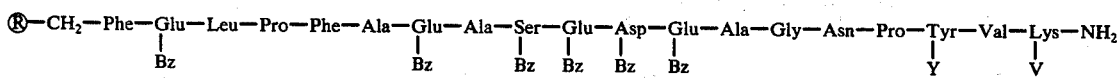

For the coupling of the arginine amino acid in reaction No. 22 at position 18 we prefer to use as the guanidino protection agent that tosyl group (p-toluene sulfonyl) but may use a nitro group, and in the formula of this specification we employ the symbol T to mean tosyl or nitro. We also use the T protection group in joining arginine in reaction 23 at position 17, and in reaction 32 at position 8.

To illustrate, the structural formula for Compound No. 22 formed as a result of reaction No. 22, is given as follows:

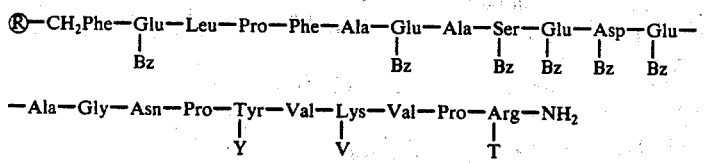

For the coupling of the histidine in reaction No. 34 at position 6, we prefer to use as the imidazole protection agent the carbobenzyloxy group (CBZ) but may use as tosyl, dinitrophenyl, benzyl, benzyl derivative or no protecting group. We use the symbol W to indicate either no protective group or any of the above named derivatives.

The symbols T, Y, V and W have the meanings as above defined whereever they appear throughout this specification and claims.

To illustrate, the structural formula for Compound No. 34, formed as a result of reaction No. 34, is given as follows:

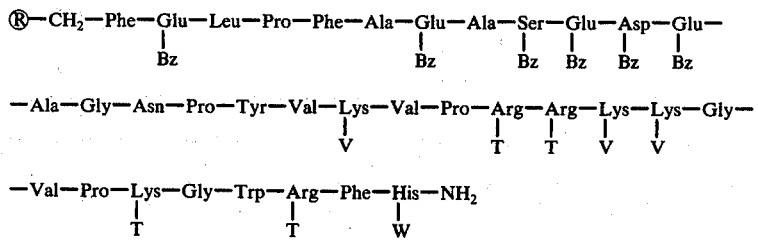

Upon the attachment of serine in reaction 39 at the number one position, according to the manner and sequence above described, and the deprotection and neutralization of the coupled resin peptide, we arrive at Compound No. 39 which has the following formula:

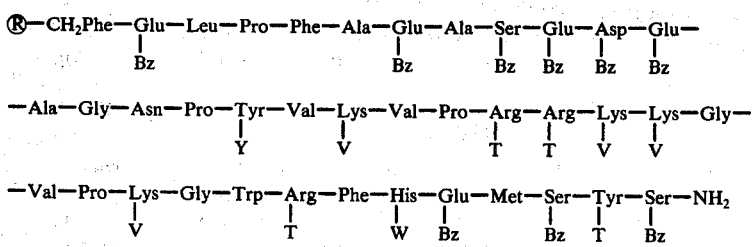

After each coupling reaction, and before deprotection of the resin peptide we prefer to apply the Ninhydrin test, and we find the test is not always negative requiring a repeat of the coupling reaction last performed.

As an example, we found that when 25 grams of BOC-phenylalanine resin was subjected to reactions 2 to 39 of Table 1 the resulting Compound No. 39 (after deprotection, neutralization and drying under vacuum) weighed 53.0 grams.

After the synthesis of the resin peptide and the attachment of all the desired amino acids in the desired sequence, this resin peptide, after the usual deprotection and neutralization steps, may be treated to remove the resin and the remaining protective groups. Suitably, the resin and most or all of the remaining protective groups may be removed by treatment with hydrogen fluoride. The formula for this cleavage reaction is:

lation, the residue washed 4 times with ethyl acetate followed by extraction with glacial acetic acid. The

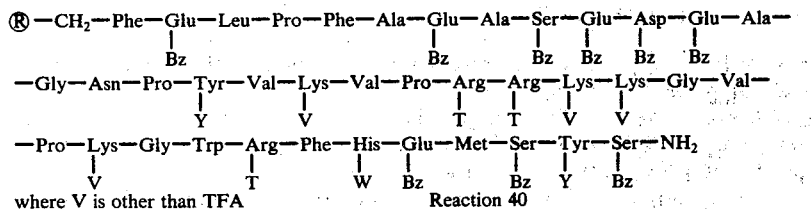
where V is other than TFA    Reaction 40

+ HF

↓

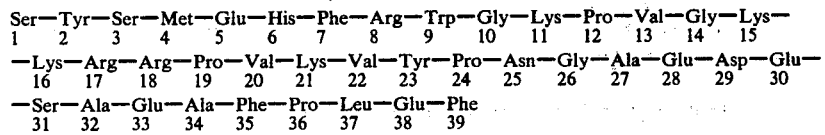

which we call Compound 40.

Where V in the above reaction is TFA the reaction product is:

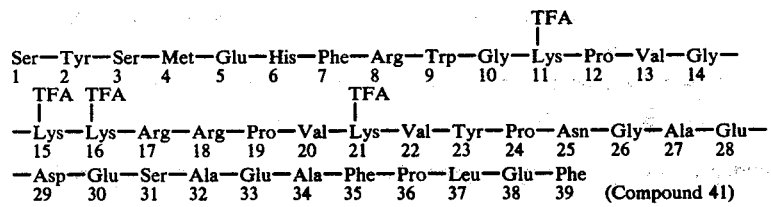
(Compound 41)

The following Example 6 gives a specific demonstration of the cleavage reaction above referred to where V is other than TFA.

EXAMPLE 6

Two grams of compound 39 were placed in a Kel-F vessel with 2 mls of anisole and 10 mls of anhydrous hydrogen fluoride was added by distillation. This mixture was stirred at 0° C for 1 hour. The hydrogen fluoride was removed by vacuum distillation, the residue washed four times with ethyl acetate followed by extraction with glacial acetic acid. The acetic acid extract was lyophilized to give 0.86 grams of a fluffy white powder. This process removes the peptide from the resin and removes all protective groups on the amino acid.

The following Example 7 gives a specific demonstration of the cleavage reaction above referred to where V is TFA.

EXAMPLE 7

Two grams of the above blocked ACTH resin peptide were placed in a Kel-F vessel with 2 ml of anisole and 10 mls of anhydrous hydrogen fluoride was added by distillation. This mixture was stirred at 0° C for 1 hour. The hydrogen fluoride was removed by vacuum distilacetic acid extract was lyophilized to give 856 mg of fluffy white powder. This process removes the peptide from the resin and removes all blocking groups on the difunctional amino acids except the trifluoroacetyl blocking groups of the lysine residues. Hence, this product is called TFA-ACTH peptide.

The TFA-ACTH peptide was treated with aqueous ammonium hydroxide for removal of the trifluoroacetyl groups from the lysine residue. Three hundred eighty mg of the TFA-ACTH was stirred with 100 ml of 4 normal ammonium hydroxide containing 0.1% mercaptoethanol for 16 hours. This generates the crude ACTH which had an ACTH activity of 40 units per mg when assayed by the U.S.P. method.

We have further discovered a synthesis of an active ACTH hormone of a sequence described by T. H. Lee, A. B. Lerner and V. Buettner — Janusch, J. Biol. Chem., 236,2970 (1961) (glutamine sequence) which we believe to be an improvement on the asparagine sequence ACTH hormone the synthesis of which has above been described. This peptide is easier to purify and is more alkali stable than the peptide having the asparagine sequence. This synthesis involves coupling of different amino acids at certain coupling reactions. These differences will become more apparent on reference to the following Table II which describes the coupling reactions of the synthesis of the glutamine sequence, when using preferred protecting groups.

TABLE II

| Reaction Number | Position Number | Amino Acid Being Attached | Amino Acid Group with Preferred Protectants |
|---|---|---|---|
| 10 | 30 | glutamine | BOC-*l*-glutamine-p-nitrophenylester |

TABLE II-continued

| Reaction Number | Position Number | Amino Acid Being Attached | Amino Acid Group with Preferred Protectants |
|---|---|---|---|
| 11 | 29 | aspartic acid | BOC-*l*-β-benzyl aspartate |
| 12 | 28 | glutamic acid | BOC-*l*-δ-benzyl glutamate |
| 13 | 27 | glycine | BOC-glycine |
| 14 | 26 | alanine | BOC-*l*-alanine |
| 15 | 25 | aspartic acid | BOC-*l*-β-benzyl aspartate |
| 16 | 24 | proline | BOC-*l*-proline |
| 17 | 23 | tyrosine | BOC-*l*-tyrosine (20% dimethylformamide for solubility) |
| 18 | 22 | valine | BOC-*l*-valine |
| 19 | 21 | lysine | BOC-e-trifluoro-acetyl-*l*-lysine (5% dimethylformamide for solubility) |
| 20 | 20 | valine | BOC-*l*-valine |
| 21 | 19 | proline | BOC-*l*-proline |
| 22 | 18 | arginine | BOC-*l*-tosylarginine (20% dimethylformamide for solubility) |
| 23 | 17 | arginine | BOC-*l*-tosylarginine (20% dimethylformamide for solubility) |
| 24 | 16 | lysine | BOC-e-trifluoracetyl-*l*-lysine (5% dimethylformamide for solubility) |
| 25 | 15 | lysine | BOC-e-trifluoracetyl-*l*-lysine (5% dimethylformamide for solubility) |
| 26 | 14 | glycine | BOC-glycine |
| 27 | 13 | valine | BOC-*l*-valine |
| 28 | 12 | proline | BOC-*l*-proline |
| 29 | 11 | lysine | BOC-e-trifluor-acetyl-*l*-lysine (5% dimethylformamide for solubility) |
| 30 | 10 | glycine | BOC-glycine |
| 31 | 9 | tryptophan | BOC-*l*-tryptophan |
| 32 | 8 | arginine | BOC-*l*-tosylarginine (20% dimethylformamide for solubility) |
| 33 | 7 | phenylalanine | BOC-*l*-phenylalanine |
| 34 | 6 | histidine | BOC-im-carbobenzyloxy-*l*-histidine |
| 35 | 5 | glutamic acid | BOC-*l*-δ-benzyl glutamate |
| 36 | 4 | methionine | BOC-*l*-methionine |
| 37 | 3 | serine | BOC-O-benzyl-*l*-serine |
| 38 | 2 | tyrosine | BOC-*l*-tyrosine (20% dimethylformamide for solubility) |
| 39 | 1 | serine | BOC-O-benzyl-*l*-serine |

*Reactions 2 to 9 at positions 39 to 31 are precisely the same as given in Table No. 1.

As seen from the above Table II, our improved synthesis differs in that different amino groups are attached at the 30th, the 27th, the 26th and the 25th positions in the amino acid chain. Compounds 1 to 9 of this synthesis are the same as compounds 1 to 9 of the synthesis first described, but in reaction No. 10, where Gln is substituted for Glu the resulting compound which we will call 10A has the formula:

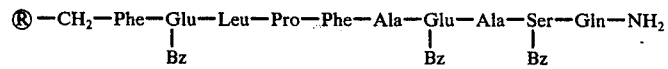

in the reaction No. 13, where Gly is substituted for Ala, the resulting compound, which we call Compound 13A, has the formula:

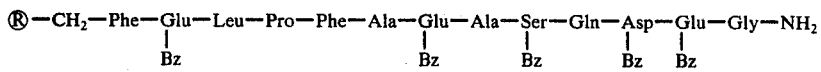

in reaction No. 14, where Ala is substituted for Gly, the resulting resin peptide, which we call compound 14A, has the following formula:

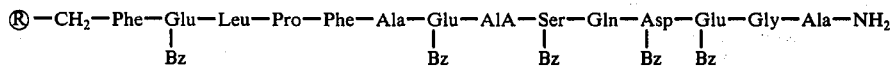

in reaction No. 15, where Asp is substituted for Asn, the resulting resin peptide, which we call compound 15A, has the following formula:

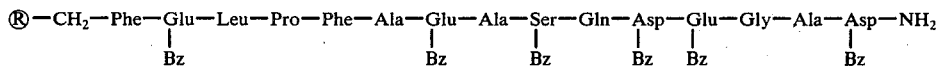

and the final coupling reaction No. 39 results in a resin peptide which we call Compound 39A, having the following formula:

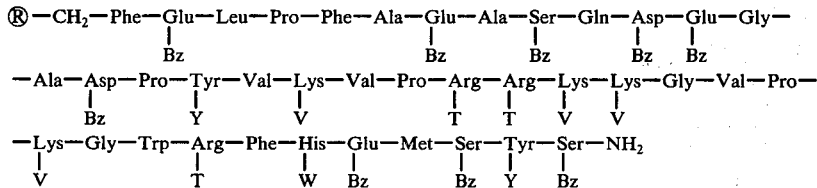

When Compound 39A (where V is TFA) is subjected to treatment with HF, it becomes:

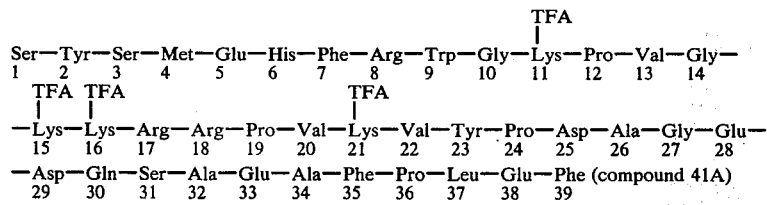

and when treated with a suitable aqueous base such as piperidine or ammonium hydroxide, to remove the TFA groups, becomes:

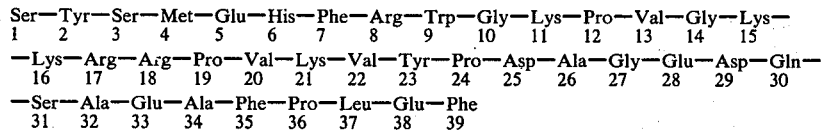

In cases where V is other than TFA, and when the Compound 39A is subjected to treatment with HF this compound becomes the Compound 42, with the structure above given. Compound 42 may be purified as described in connection with Compound 40, and is found to be biologically active as an ACTH hormone.

EXAMPLE 8

In this specific example we record the synthesis, on a medium scale, of Compound 42, and its purification to obtain a biologically effective ACTH hormone product.

Twenty-five grams of BOC-phenylalanine resin prepared as reaction No. 1, previously described, was placed in the reaction vessel of a peptide synthesizer marketed by Schwarz-Mann, Inc., of Orangeburg, New York. This apparatus is for the automated synthesis of peptides by a tape reading programmer. The resin used had a 0.397 meq/gm equivalency and 9.927 total milliequivalents. The system of coupling, deprotection and neturalization were as follows:

Coupling:

25 millimoles of appropriate amino acid (1.5 equivalent excess) dissolved in 25 ml dimethylformamide, 25 ml anisole, 25 grams urethane and 75 ml of methylene chloride - 10 min. stirring 25 millimoles of dicyclohexylcarbodiimide in 70 ml of trichloroethylene - reaction time with stirring for 45 min.

3X 150 ml - methylene chloride - 2 min. each
3X 150 ml - methanol - 2 min. each 2X 150 ml - trichlorethylene - 2 min. each Deprotection:

2X 150 ml - trichloroethylene washes - 2 min. each 75 ml 20% phenol in 4N-HCl dioxane +75 ml 50% trichloroacetic acid in trichloroethylene with 4% mercaptoethanol for 30 min.

2X 150 ml - chloroform - 2 min. each
2X 150 ml - methanol - 2 min. each
3X 150 ml - chloroform - 2 min. each Neutralization:

1X 150 ml - 10% triethylamine in chloroform - 10 min.
4X 150 ml - chloroform - 2 min. each The amino acids were coupled in the order set forth in Table II, and using the same combined amino acid and protecting groups as set forth in Table II.

In reaction 10 at position 30 the resin was washed three times with dimethylformamide and after the neutralization step, 25 millimoles of BOC-l-glutamine-p-nitrophenylester dissolved in 150 ml of dimethylformamide containing 1% acetic acid, was added and allowed to react for 16 hours. The resin was then washed with three portions of dimethylformamide, two minutes each, with two portions of methanol, two minutes each, and with three trichloroethylene, two minutes each.

The resin was subjected to the Ninhydrin Test after each coupling and this gave a positive result at the reaction 17 but gave a negative result after this reaction was repeated. Upon completion of the 39 coupling reactions and after final deprotection and neutralization and drying under vacuum the yield was 40.5 grams.

Two grams of the protected resin peptide was reacted with hydrogen fluoride and anisole as previously described. The yield was 822 mg of the peptide having TFA protecting groups still attached. A similar 4 gram cleavage gave 1,685 mg.

To purify the peptide compound, 1.35 grams of the peptide separate from the resin but still retaining its TFA groups was stirred with 135 ml of 0.2 molar piperidine containing 0.1% mercaptoethanol for 2 hours. This mixture was lypholized to give an off-white solid. This mixture was dissolved in 100 ml water and adjusted to pH 4.5 with acetic acid and absorbed on a carboxymethyl cellulose column of 750 ml bed volume. The impurities were eluted with 18 bed volumes of 8 mmho ammonium acetate buffer at pH 6.7. The active ACTH peak was then eluted with 11.5 mmho buffer at pH 6.7. The active fractions were lyophilized and desalted on a column of G-25 fine Sephadex. The lyophilized white fluffy powder yield was 361 mg. It had an ACTH activity of 92±11 units per milligram and had the correct amino acid composition.

EXAMPLE 9

In this specific example we record the synthesis, on a large scale, of compound 41A and its purification to obtain a biologically effective ACTH hormone product.

116.5 grams of BOC-phenylalanine resin was placed in a specially built reactor for Schwarz-Mann Peptide Synthesizer. This resin had a titer of 0.57 meq/gm or 66.4 meq total. In this synthesis the coupling, deprotection, and neutralization steps were as follows:

Coupling:
- 133 millimoles of appropriate BOC amino acid (1 equivalent excess) dissolved in 600 ml of methylene chloride - 10 min. stirring
- 133 millimoles of dicyclohexylcarbodiimide in 133 ml of methlene chloride - 45 min. reaction time
- 2X 750 ml - methylene chloride - 2 min. each
- 2X 750 ml - methanol - 2 min. each
- 3X 750 ml - methylene chloride - 2 min. each Deprotection:
- 2X 750 ml - methylene chloride - 2 min. each
- 50-50 mixture of trifluoroacetic acid and methylene chloride - 30 min. 750 ml
- 3X 750 ml - methlene chloride - 2 min. each
- 3X 750 ml - methanol - 2 min. each Neutralization:
- 2X 750 ml - 10% triethylamine in chloroform - 5 min. each
- 2X 750 ml - chloroform - 2 min. each
- 2X 750 ml - methlene chloride - 2 min. each The sequence of the amino acids, the combined amino groups and protective groups and the procedures followed were the same as in Example 8.

The Ninhydrin Test was applied at each coupling reaction and found to be positive at each of reactions Nos. 2, 22 and 23, but in each case the test showed negative after repeating the coupling step.

In reaction No. 10 at position 30, the coupling involved the use of the p-nitrophenyl active ester as in Example 8.

The yield of the resin peptide (Compound No. 39A) after the final, or 39th, coupling and after deprotection, neutralization and drying under vacuum was 316 grams.

Cleavage 100 grams of the above resin peptide was placed in a large scale Kel-F vessel with 5 grams of dithioerythritol and 100 ml of anisole. 350 ml of anhydrous hydrogen fluoride was added by distillation and the mixture stirred at 0° C for 20 minutes. Then the hydrogen fluoride was removed by vacuum distillation. The residue was washed four times with 1 liter portions of ethyl acetate followed by extraction with glacial acetic acid. The acetic acid extract was lyophilized to give 47.6 grams of a fluffy white powder which is Compound 41A still retaining the TFA groups.

47.6 grams of the TFA peptide (Compound 41A) was stirred for three hours in 5.5 liters of 0.2 molar piperidine and one molar urea containing 0.1% mercaptoethanol. This solution was then adjusted to pH 4.0 with acetic acid and filtered through an 0.22 micron millipore filter. This solution was then ready for purification.

Purification

The crude ACTH peptide, with the resin and all protecting groups removed, was absorbed on a column of carboxymethyl cellulose with a bed volume of 1800 ml. The impurities were eluted with 44 liters of ammonium acetate buffer at pH 6.7 and 4.0 mmhos. The ACTH peak was eluted with ammonium acetate buffer at pH 7.5 and 4.0 mmhos and lyophilized to a white powder. This power was dissolved in 400 ml of 0.5 molar acetic acid containing 0.1% mercaptoethanol and desalted on a column of 16 liters bed volume of Sephadex G-25 superfine. The peptide containing peak was lyophilized to give 7.19 grams of fluffy white powder with the correct amino acid composition and an ACTH activity of 82±7 units per milligram.

While only certain embodiments of our invention have been described in specific detail it will be apparent to those skilled in this art that other specific embodiments may be practiced, and many changes made all within the spirit of the invention, and it is intended that all such other embodiments and changes be considered within the scope of the appended claims.

We claim:

1. A resin peptide having the structure:

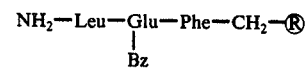

in which
Bz is benzyl, p-methoxybenzyl, p-chlorobenzyl, p-nitrobenzyl or benzylhydryl and
Ⓡ is divinylbenzene crosslinked polystyrene resin.

2. A resin peptide having the structure:

$$\text{NH}_2-\text{Phe}-\text{Pro}-\text{Leu}-\underset{\underset{\text{Bz}}{|}}{\text{Glu}}-\text{Phe}-\text{CH}_2-\circledR$$

in which
- Bz is benzyl, p-methoxybenzyl, p-chlorobenzyl, p-nitrobenzyl or benzylhydryl and
- ⓡ is divinylbenzene crosslinked polystyrene resin.

3. A resin peptide having the structure:

$$\text{NH}_2-\underset{\underset{\text{T}}{|}}{\text{Arg}}-\text{Trp}-\text{Gly}-\underset{\underset{\text{V}}{|}}{\text{Lys}}-\text{Pro}-\text{Val}-\text{Gly}-\underset{\underset{\text{V}}{|}}{\text{Lys}}-\underset{\underset{\text{V}}{|}}{\text{Lys}}-\underset{\underset{\text{T}}{|}}{\text{Arg}}-\underset{\underset{\text{T}}{|}}{\text{Arg}}-\text{Pro}-\text{Val}-$$

$$\underset{\underset{\text{V}}{|}}{\text{Lys}}-\text{Val}-\underset{\underset{\text{Y}}{|}}{\text{Tyr}}-\text{Pro}-\text{Asn}-\text{Gly}-\text{Ala}-\underset{\underset{\text{Bz}}{|}}{\text{Glu}}-\underset{\underset{\text{Bz}}{|}}{\text{Asp}}-\underset{\underset{\text{Bz}}{|}}{\text{Glu}}-\underset{\underset{\text{Bz}}{|}}{\text{Ser}}-\text{Ala}-\underset{\underset{\text{Bz}}{|}}{\text{Glu}}-\text{Ala}-$$

$$\text{Phe}-\text{Pro}-\text{Leu}-\underset{\underset{\text{Bz}}{|}}{\text{Glu}}-\text{Phe}-\text{CH}_2-\circledR$$

in which
- Bz is benzyl, p-methoxybenzyl, p-chlorobenzyl, p-nitrobenzyl or benzylhydryl,
- Y is Bz or H
- V is 2-chlorocarbobenzyloxy, carbobenzyloxy, 2-bromocarbobenzyloxy, 2-4-dichlorocarbobenzyloxy or trifluoroacetyl,
- T is tosyl or nitro, and
- ⓡ is divinylbenzene crosslinked polystyrene resin.

4. A resin peptide having the structure:

$$\text{NH}-\underset{\underset{\text{Bz}}{|}}{\text{Asp}}-\text{Ala}-\text{Gly}-\underset{\underset{\text{Bz}}{|}}{\text{Glu}}-\underset{\underset{\text{Bz}}{|}}{\text{Asp}}-\text{Gln}-\underset{\underset{\text{Bz}}{|}}{\text{Ser}}-\text{Ala}-\underset{\underset{\text{Bz}}{|}}{\text{Glu}}-\text{Ala}-\text{Phe}-\text{Pro}-\text{Leu}-\underset{\underset{\text{Bz}}{|}}{\text{Glu}}-$$

$$\text{Phe}-\text{CH}_2-\circledR$$

in which
- Bz is benzyl, p-methoxybenzyl, p-chlorobenzyl, p-nitrobenzyl or benzylhydryl,
- ⓡ is divinylbenzene crosslinked polystyrene resin,
- Y is Bz or H and
- V is 2-chlorocarbobenzyloxy, carbobenzyloxy, 2-bromocarbobenzyloxy, 2,4-dichlorocarbobenzyloxy or trifluoracetyl.

5. A resin peptide having the structure:

$$\text{NH}_2-\text{Gly}-\underset{\underset{\text{V}}{|}}{\text{Lys}}-\underset{\underset{\text{T}}{|}}{\text{Arg}}-\underset{\underset{\text{T}}{|}}{\text{Arg}}-\text{Pro}-\text{Val}-\underset{\underset{\text{V}}{|}}{\text{Lys}}-\text{Val}-\text{Tyr}-\text{Pro}-\underset{\underset{\text{Bz}}{|}}{\text{Asp}}-\text{Ala}-\text{Gly}-$$

$$\underset{\underset{\text{Bz}}{|}}{\text{Glu}}-\underset{\underset{\text{Bz}}{|}}{\text{Asp}}-\underset{\underset{\text{Bz}}{|}}{\text{Gln}}-\underset{\underset{\text{Bz}}{|}}{\text{Ser}}-\text{Ala}-\underset{\underset{\text{Bz}}{|}}{\text{Glu}}-\text{Ala}-\text{Phe}-\text{Pro}-\text{Leu}-\underset{\underset{\text{Bz}}{|}}{\text{Glu}}-\text{Phe}-\text{CH}_2-\circledR$$

in which
- Bz is benzyl, p-methoxybenzyl, p-chlorobenzyl, p-nitrobenzyl or benzylhydryl,
- ⓡ is divinylbenzene crosslinked polystyrene resin,
- Y is Bz or H,
- V is 2-chlorocarbobenzyloxy, carbobenzyloxy, 2-bromocarbobenzyloxy, 2-4-dichlorocarbobenzyloxy or trifluoroacetyl, and
- T is tosyl or nitro.

6. A resin peptide as set forth in claim 1 in which Bz is benzyl.

7. A resin peptide as set forth in claim 2 in which Bz is benzyl.

8. A resin peptide as set forth in claim 3 in which Bz is benzyl.

9. A resin peptide as set forth in claim 4 in which Bz is benzyl.

10. A resin peptide as set forth in claim 3 in which T is tosyl.

11. A resin peptide as set forth in claim 3 in which V is trifluoracetyl and Bz is benzyl.

12. A resin peptide as set forth in claim 4 in which V is trifluoracetyl and Bz is benzyl.

13. A resin peptide as set forth in claim 4 in which T is tosyl.

* * * * *